United States Patent [19]

deBerardinis et al.

[11] 4,292,451

[45] Sep. 29, 1981

[54] HIGH MANNITOL PROCESS (ALKALINE HYDROGENATION IN PRESENCE OF ALKALI METAL CARBONATE)

[75] Inventors: Albert J. deBerardinis; Walter M. Kruse, both of New Castle County, Del.

[73] Assignee: ICI Americas Inc., Wilmington, Del.

[21] Appl. No.: 57,397

[22] Filed: Jul. 13, 1979

Related U.S. Application Data

[63] Continuation-in-part of Ser. No. 891,712, Mar. 30, 1978, abandoned.

[51] Int. Cl.$^3$ .................... C07C 31/26; C12P 19/24
[52] U.S. Cl. ........................ 568/863; 435/94
[58] Field of Search ............ 568/863; 435/94

[56] References Cited

U.S. PATENT DOCUMENTS

| | | |
|---|---|---|
| 1,990,245 | 2/1935 | Mueller et al. |
| 2,004,135 | 6/1935 | Rothrock |
| 2,642,462 | 6/1953 | Kasehagen ............... 568/863 |
| 2,989,569 | 6/1961 | Apel |
| 3,763,246 | 10/1973 | Berardinis ............... 568/863 |
| 4,029,878 | 6/1977 | Kruse ............... 568/863 |
| 4,083,881 | 4/1978 | Takemura et al. ............... 568/863 |
| 4,173,514 | 11/1979 | Kruse ............... 435/94 |

FOREIGN PATENT DOCUMENTS

| | | |
|---|---|---|
| 544666 | 2/1932 | Fed. Rep. of Germany . |
| 1300918 | 7/1967 | Fed. Rep. of Germany . |
| 1931112 | 6/1969 | Fed. Rep. of Germany . |
| 1198373 | 6/1959 | France . |
| 2335479 | 7/1977 | France . |
| 404628 | 7/1966 | Switzerland . |
| 354196 | 8/1931 | United Kingdom . |
| 838766 | 6/1960 | United Kingdom . |
| 883812 | 12/1961 | United Kingdom ............... 568/863 |
| 1025813 | 4/1966 | United Kingdom ............... 568/863 |
| 1931112 | 6/1969 | Fed. Rep. of Germany . |

OTHER PUBLICATIONS

Bilik et al., "Angew. Chem.", International Edition in English, vol. 10, Jul.–Dec. 1971, p. 909.
Bilik, "Chem. Abstracts", vol. 79, (1973) 146807w.
Takemura et al., "Chem. Abstracts", vol. 85 (1976) 107492u.

*Primary Examiner*—Joseph E. Evans

[57] ABSTRACT

Sugar mixtures comprising glucose and either mannose, or both, are catalytically hydrogenated in aqueous solution containing 0.2–1.5% by weight (based on sugar) of sodium carbonate or other basic reacting alkali metal salt, yielding mannitol-rich solutions of sorbitol and mannitol. Hydrogenation is preferably carried out in two stages, the first at temperature of about 60°–100° C., the second at temperatures of about 110°–160° C.

12 Claims, No Drawings

HIGH MANNITOL PROCESS (ALKALINE HYDROGENATION IN PRESENCE OF ALKALI METAL CARBONATE)

CROSS REFERENCE TO RELATED APPLICATION

This application is a continuation-in-part of our copending application Ser. No. 891,712 filed Mar. 30, 1978, now abandoned.

BACKGROUND OF THE INVENTION

The present invention relates to a process for producing mannitol-rich solutions of sorbitol and mannitol. More particularly, this invention relates to a process for producing a mannitol-rich solution of sorbitol and mannitol from glucose.

It is well known that a mixture of sorbitol and mannitol in aqueous solution can be produced by catalytic hydrogenation of invert sugar, which is an approximately equimolar mixture of glucose and fructose. Invert sugar, in turn, is commonly obtained by inversion of sucrose (ordinary sugar). The yield of mannitol is ordinarily about 24–26 percent by weight, based on total dry solids, when hydrogenation is carried out under neutral or mildly acidic conditions, such as those disclosed in U.S. Pat. No. 2,759,024 to Kasehagen. This yield can be increased by carrying out at least part of the hydrogenation under alkaline conditions, as described in U.S. Pat. Nos. 3,329,729 to Brandner et al and 3,763,246 to deBerardinis, or by appropriate choice of catalyst, as described in U.S. Pat. No. 3,705,199 to deBerardinis, or both. The processes of U.S. Pat. Nos. 3,329,729 and 3,763,246 are plural stage processes in which alkaline hydrogenation is followed by acid hydrogenation. Alkaline agents for the alkaline hydrogenation stages of those processes are alkali metal hydroxides such as sodium hydroxide, and alkaline earth metal oxides and hydroxides such as lime. U.S. Pat. No. 3,329,729 also suggests the addition of calcium carbonate as a buffering agent in addition to lime. Mannitol yields (in percent by weight on the dry basis) are as follows: U.S. Pat. Nos. 3,329,729, 30–36%; 3,705,199, 28–29%; 3,763,246, 27–31%. In each case the balance of the reaction product is mostly sorbitol.

Enhanced yields of mannitol under alkaline hydrogenation conditions are due to isomerization of part of the glucose present to fructose and mannose. The proportions of glucose, fructose, and mannose in the reaction mixture will vary depending on the alkaline material and the conditions used, and significant quantities of mannose are not ordinarily obtained. Such isomerization is well known in the art, and is discussed, for example, in U.S. Pat. Nos. 3,329,729 and 3,763,246 cited supra, and in Pigman, "The Carbohydrates: Chemistry, Biochemistry, and Physiology," Academic Press, New York 1957, pages 60–69.

High cost of mannose and fructose in substantially pure form preclude the economic use of these sugars as starting materials, even though mannose yields essentially pure mannitol and fructose yields a 50:50 mixture of sorbitol and mannitol on catalytic hydrogenation in neutral media.

Hydrogenation of either glucose or mannose in the presence of a platinum catalyst and considerable alkali yields a mixture of sorbitol and mannitol, according to U.S. Pat. No. 1,990,245 to Mueller et al. This reference also states, however, that pure sorbitol is obtained when glucose is hydrogenated at a pH from 7 to 12 in the presence of a nickel catalyst. The reaction medium is made alkaline by the addition of an alkali or alkaline earth metal oxide, hydroxide, or alkaline reacting salt such as a carbonate, silicate, or borate. Other references teach that hydrogenation of glucose in the presence of a nickel catalyst yields a mixture of sorbitol and mannitol under strongly alkaline conditions (pH 10 or over; British Pat. No. 1,129,586), while substantially pure sorbitol is obtained under milder alkaline conditions (pH 8.3–8.5; British Pat. No. 1,140,477). Canadian Pat. No. 735,972 to Silber describes catalytic hydrogenation of glucose and invert sugar to mixtures of sorbitol and mannitol in aqueous solution which is made alkaline with lime and optionally also with calcium carbonate. Glucose is hydrogenated substantially quantitatively to sorbitol under neutral or mildly acidic conditions; see U.S. Pat. Nos. 1,963,999 to Larchar and 2,280,975 to Power.

A process for obtaining sorbitol-mannitol solutions from glucose by first catalytically epimerizing glucose in an acidic aqueous solution containing at least 50% by weight of glucose to obtain an epimerizate of glucose and mannose, and then catalytically hydrogenating this epimerizate to obtain an aqueous solution of sorbitol and mannitol, is described in U.S. Pat. No. 4,029,878 to Kruse. Epimerization according to that process is carried out at elevated temperature in the presence of a hexavalent molybdenum catalyst, such as molybdic acid or an anion exchange resin in the molybdate form. Hydrogenation catalysts and conditions for hydrogenating the glucose-mannose epimerizate to a mixture of sorbitol and mannitol in that process are conventional. Ordinarily the epimerizate will contain about 30% (e.g., about 27–33%) of mannose on the dry basis, and the mol percentage of mannitol in the final product is also usually about 30%; that is, the mol percentage of mannitol in the final product does not differ significantly from the mol percentage of mannose in the epimerizate.

Production of sorbitol-mannitol mixtures in a process which comprises the successive steps of epimerizing glucose in aqueous solution containing a hexavalent molybdenum catalyst, treating the epimerizate with glucose isomerase enzyme under isomerizing conditions, and hydrogenating the resulting sugar mixture (a mixture of glucose, mannose, and fructose in aqueous solution) under non-alkaline conditions, is described in Japanese Patent Publication 51-75008. The product contains approximately 40% by weight (dry basis) of mannitol, balance principally sorbitol.

Mannitol may be recovered from aqueous solutions containing both sorbitol and mannitol by fractional crystallization, as described for example in U.S. Pat. No. 3,632,656.

Although yields of mannitol can be enhanced by hydrogenating either glucose or invert sugar under alkaline conditions rather than under neutral or mildly acidic conditions, quantities of impurities are also greater when alkaline conditions are used. There is a need for a hydrogenation process in which enhanced mannitol yields are obtained while at the same time the amounts of impurities are minimized.

SUMMARY

It has been found, according to the present invention, that a mannitol-rich aqueous solution of sorbitol and mannitol is produced by hydrogenating a sugar mixture comprising glucose and mannose in aqueous solution with hydrogen in the presence of a hydrogenation catalyst under hydrogenation conditions, the solution of the sugar mixture containing an alkali metal salt of a weak acid in sufficient quantity so that the percentage of mannitol in the mannitol-rich solution exceeds the percentage of mannitol which would be obtained from hydrogenation of the sugar mixture under non-isomerizing conditions.

DESCRIPTION OF THE PREFERRED EMBODIMENTS

The starting materials for the process of this invention are aqueous solutions comprising glucose and mannose. Starting materials include glucose-mannose and glucose-mannose-fructose solutions. The quantities of disaccharides and higher oligosaccharides in the starting solution are as small as possible, since oligosaccharides (including disaccharides) result in impurities in the final sorbitol-mannitol product. The starting solutions should contain only small amounts, preferably not more than 2 percent and more preferably not more than one percent by weight on the dry basis, of oligosaccharides.

Aqueous solutions of glucose and mannose are the preferred starting materials. Such solution can be prepared by catalytic epimerization of glucose in aqueous solution. Procedures for catalytic epimerization of glucose are known in the art, and are described, for example, in U.S. Pat. No. 4,029,878 to Kruse (one of the inventors herein), in Takemura et al., Japanese Patent Publication No. 51-75008 (1976), and in Bilik, *Chem. Zvesti*, 26, 183–186 (1972). According to these references, glucose is contacted with an epimerization catalyst (e.g., molybdic acid) under epimerization conditions, producing a solution containing a major amount (on the dry basis) of glucose and a minor amount of mannose.

Glucose is preferably epimerized as described in U.S. Pat. No. 4,029,878, previously cited, the disclosure of which is incorporated by reference. Although any of the catalysts, catalyst concentrations, temperatures, and other reaction conditions described in U.S. Pat. No. 4,029,878 can be used, it is preferred to epimerize glucose in a 50 to 70% (by weight) aqueous solution which also contains molybdic acid in an amount of about 0.25 percent by weight, based on the initial weight of glucose, and which has a pH of about 3.5–4, at temperatures of about 90°–100° C. and at atmospheric pressure for about 3 hours. The epimerized glucose products obtained under these conditions usually contain about 25–32 percent by weight of mannose, from a trace up to about 2 percent by weight of oligosaccharides (including disaccharides), balance essentially glucose, on the dry basis. Epimerization temperatures in the 90°–100° C. range give epimerizates containing smaller amounts of disaccharides than those obtained at higher temperatures. Disaccharide formation can be held to a minimum (about 0.5 percent by weight or less on the dry basis) by using epimerization temperatures below about 95° C. Mannose yields obtained at temperatures below 95° C. are slightly lower (about 25–28 percent dry basis) than those obtained at 95°–100° C.; however, the smaller amounts of disaccharides result in a final sorbitol-mannitol product of higher quality. Catalyst concentrations greater or less than 0.25 percent, and reaction times which are either longer or shorter than 3 hours, can be used; the amounts of mannose and disaccharides in the epimerizate are less sensitive to small changes in catalyst concentration and reaction time than to small changes in temperature.

Alternatively, one may use the procedure described by V. Bilik in *Chem. Zvesti*, 26, 183–186 (1972). Bilik describes a procedure in which a 25 percent yield of mannose at equilibrium is obtained by epimerizing at 90° C. an aqueous solution containing about 17 percent by weight of glucose (i.e., 20 grams of glucose per 100 ml of water) and also containing dissolved molybdic acid in an amount of 1 percent based on glucose (i.e., 200 mg per 100 ml of water). Epimerization according to the process of U.S. Pat. No. 4,029,878, rather than according to Bilik's process, is preferred because, first, a higher yield of mannose is obtained in that process, and secondly, because the higher solids concentrations used in that process make it unnecessary to handle or to evaporate large quantities of water in subsequent process steps.

The glucose-mannose solution obtained on epimerization is purified in order to remove the molybdenum catalyst, other ions, and other impurities such as color bodies. This may be done by contacting the solution with a cation exchange resin and an anion exchange resin, and with one or more adsorbents, such as an adsorbent resin, activated carbon, or both. The epimerizate solution is preferably diluted with water where necessary to a solids content of about 50–60% prior to treatment. The preferred cation exchange resins are strongly acid resins, such as "Permutit Q-4" sulfonated styrene-divinylbenzene resin made by Permutit Co. division of Sybron Corp., Paramus, N.J. The preferred anion exchange resin is "Amberlite XE-275" resin, a weakly basic macroretricular acrylic resin having tertiary amine functionality, made by Rohm and Haas Company, Philadelphia, Pa. Examples of suitable decolorizing materials are "Duolite S-30" resin, which is made by Diamond Shamrock Chemical Corporation of Redwood City, Calif., and "Darco S-51" activated carbon which is made by ICI Americas Inc. of Wilmington, Del. A preferred treatment procedure comprises treatment of the diluted epimerizate with decolorizing resin (e.g., "Duolite S-30" resin), a strongly acid cation exchange resin (e.g., "Permutit Q-4" resin), a weakly basic anion exchange resin (e.g., "Amerblite XE-275" resin), a second portion of strongly acid cation exchange resin (e.g., "Permutit Q-4" resin), a second portion of weakly basic anion exchange resin (e.g., "Amberlite XE-275" resin) and activated carbon (e.g., "Darco S-51") in the order named. It is necessary to remove molybdenum since hydrogenation catalysts tend to be sensitive to the presence of molybdenum. The treated solution is essentially neutral, and may have a slightly lower solids content that the untreated solution (say 50% vs. 55% solids).

According to this invention the purified glucose-mannose epimerizate mixture is catalytically hydrogenated in an aqueous solution which is made alkaline by the presence of an alkali metal salt of a weak acid, yielding a reaction product mixture of sorbitol, mannitol, and minor amounts of impurities. The quantity of alkali metal salt in solution is sufficient so that the quantity of mannitol in the reaction product is greater than the quantity of mannitol which would be obtained under non-isomerizing (i.e., essentially neutral or mildly acidic) hydrogenation conditions.

The epimerizate solution is made alkaline by the presence of an alkaline reacting alkali metal salt. Sodium carbonate is the preferred alkali metal salt. Other water soluble alkali metal salts which give an alkaline reaction in aqueous media, such as trisodium phosphate, can also be used. Potassium salts and other alkali metal salts can also be used in place of the corresponding sodium salts, although the sodium salts are ordinarily preferred by reason of cost. The alkali metal salt may be added to the solution where necessary after purification and before hydrogenation in order to adjust the solution to the desired pH. (The purified epimerizate is usually either non-alkaline or insufficiently alkaline to cause any isomerization of glucose to take place simultaneously with hydrogenation).

Sodium carbonate is ordinarily added in an amount of about 0.2% to about 1.5% by weight, based on the weight of sugar in the epimerizate. That is, for every one hundred pounds (dry basis) of sugar in the epimerizate solution, about 0.2 pound to about 1.5 pound of sodium carbonate is added. Preferred amounts of sodium carbonate are from about 0.25 to about 0.8% by weight, based on sugar. Equivalent quantities of other basically acting alkali metal salts may be added instead of sodium carbonate. In terms of pH, the amount of sodium carbonate or other alkali metal salt added is such as to produce a solution having a pH from about 8 to about 10, preferably from about 8 to about 9.

As the concentration of sodium carbonate or other alkaline reacting alkali metal salt is increased, the reaction rate increases but the percentage of impurities in the reaction product also increases. Good mannitol yields are obtainable at any alkali metal salt concentration specified above. Sodium carbonate concentrations above about 0.8 percent by weight (dry basis, based on sugar) are not ordinarily preferred because of the relatively large amount of by-products formed. A sodium carbonate concentration of about 0.6 percent by weight based on sugar is preferred on an overall basis (i.e., a combination of technical and economic considerations), since good product quality can be achieved at reasonable reaction times. From a purely technical standpoint, a lower sodium carbonate concentration, about 0.3 percent by weight (dry basis, based on sugar), is preferred, since impurities in the product are slightly less and the ion exchange load (i.e., the ion exchange capacity required for deionization of the product) is substantially lower. However, longer reaction times are required, and therefore operating costs are higher, at lower sodium carbonate concentrations.

Sodium bicarbonate may be added in addition to sodium carbonate to the epimerized glucose solution if desired. The addition of both sodium carbonate and sodium bicarbonate increases the buffer capacity of the solution; however, there does not appear to be any notable improvement either in increased mannitol yield or in reduced formation of by-products, compared to the use of sodium carbonate alone. Additionally, the ion exchange capacity needed to purify the hydrogenated solution is increased.

Other known buffers, such as a mixture of disodium phosphate and trisodium phosphate, can be added in place of sodium carbonate and sodium bicarbonate, in order to render the epimerizate solution alkaline.

Solution concentrations of up to 70% by weight of sugar solids may be used for hydrogenation. Solutions containing more than about 70% by weight of solids are too viscous for easy handling. Solution concentrations below about 50% by weight ordinarily are not preferred because the product solutions are too dilute for optimum crystallization of mannitol from the mixed mannitol-sorbitol product solution. Preferred solution concentrations are from about 50% to about 60% by weight of sugar solids. A solution concentration of about 55% by weight appears to be optimum for hydrogenation.

Conventional supported nickel catalysts which are known in the art can be used for hydrogenation according to this invention. A preferred catalyst is nickel supported on diatomaceous earth, such as that described in U.S. Pat. No. 3,705,199 to deBerardinis cited supra. Other known sugar hydrogenation catalysts, containing either nickel or ruthenium as the active catalyst metal, can be used. Examples of such other catalysts include the supported nickel catalyst described in U.S. Pat. No. 3,329,729 cited supra, and the supported ruthenium catalysts described in U.S. Pat. No. 2,868,847 to Boyers. Raney nickel can also be used as a catalyst, but the amounts of nickel required are larger, and the mannitol yields tend to be lower, than when a supported nickel catalyst is used under the same conditions of pressure, temperature, time, and alkali concentration. Nickel catalysts are ordinarily preferred because of their lower cost and lower sensitivity to trace amounts of molybdenum, compared to ruthenium catalysts. The amount of catalyst is preferably from about 0.6 to about 1.0 pound of nickel per 100 pounds of sugar. Excellent results are obtained at a nickel/sugar ratio of 0.6/100, and this ratio is especially preferred.

At least a portion of the hydrogenation according to this invention is ordinarily carried out at temperatures from about 50° to about 100° C., preferably at temperatures from about 60° to about 100° C. Hydrogenation according to the present process is preferably carried out in two stages, the first at a relatively low temperature of about 50° to about 100° C., preferably about 60° to about 100° C. for a relatively long reaction time of about 1.5 to about 2.5 hours, and the second at a relatively high temperature for a relatively short reaction time, e.g., at about 110° to about 160° C. for about 0.2 to about 0.5 hour. The reaction time required depends primarily on the reaction temperature (particularly in the first stage) and the alkali metal salt concentration. An increase in either alkali metal salt concentration or in reaction temperature results in a reduction in reaction time required. No alkaline or acid material is ordinarily added during the course of reaction. The reaction medium, which is initially alkaline (generally having a pH of about 8 to about 10) will ordinarily become less alkaline during the course of reaction and may in fact become slightly acid (the final pH may be as low as about 6).

Reaction times at temperatures below 60° C. are ordinarily too long for practical use. First stage reaction temperatures above 100° C. result in undesirably large amounts of impurities in the product and are therefore avoided. The preferred first stage reaction temperature is ordinarily from about 80° to about 95° C. especially from about 80° to about 85° C.; this range provides a desirable balance between reaction time and product impurity formation. Most of the hydrogenation and an even greater percentage of isomerization takes place during the first stage.

Hydrogenation is completed during the second stage. Temperatures and reaction times are chosen in accordance with the amount of unreduced sugar remaining at the end of the first stage. Preferred second stage hydrogenation temperatures are ordinarily in the range of about 120° to about 150° C. except when acid is added between the first and second stages. Temperatures over 150° C. are ordinarily used only when acid is added to the reaction mixture between the first and second hydrogenation stages as will subsequently be described.

Hydrogenation may be carried out in a single stage at temperatures below 100° C. (e.g., about 60°–100° C.) when high loadings of alkali metal salt, sufficient to produce an initial pH of about 9 or higher, are used. However, hydrogenation of such solutions usually results in larger by-product quantities than those obtained on hydrogenation of solutions having an initial pH in the range of 8 to about 9.

The yield of mannitol increases in general with increasing amounts of either mannose or sodium carbonate (or other alkaline reacting alkali metal salt) in the feed. Increases in the amount of sodium carbonate also result in increased quantities of by-products. The percentage of mannose in epimerized glucose feeds also affects to some extent the quality of by-product obtained, as previously explained. Substantially enhanced mannitol yields, compared to those obtainable under neutral or mildly acid hydrogenation conditions, are obtained with small quantities of impurities by using relatively low sodium carbonate concentrations.

Pressures can vary over a wide range. Ordinarily, elevated pressures from about 250 psig. up to as high as 3,000 psig. hydrogen pressure can be used, with little difference in mannitol yields or by-product formation over this range.

The process may be carried out in any suitable type of apparatus with which enables intimate contact of reactants and control of operating conditions. The hydrogenation apparatus must be pressure resistant. The process may be carried out in batch, semi-continuous, or continuous operation. Continuous operation of the hydrogenation process is ordinarily preferred.

It is desirable to treat the reaction product solution with anion and cation exchange resins in order to remove ions from the solution. A preferred deionization treatment uses a mixed bed containing about 60 percent by weight of a strongly basic anion resin and 40 percent by weight of a strongly acid cation exchange resin. The reaction product solution may also be treated with decolorizing materials, such as activated carbon, as required. The ion exchange capacity required (i.e., ion exchange load) is proportional to the total ion concentration in the product solution.

Mannitol may be recovered from sorbitol-mannitol mixtures in aqueous solution by means known in the art, for example, by fractional crystallization as described in U.S. Pat. No. 3,632,656.

A preferred mode of operation from a combination of technical and economic considerations is to hydrogenate a glucose-mannose mixture or epimerizate in aqueous solution containing about 0.6 percent by weight (based on sugar) of sodium carbonate at about 80° to about 85° C. for about 1.5 to about 1.75 hours, and then at about 140° C. for about 0.25–0.5 hour (total about 2 hours). From purely technical considerations, a lower sodium carbonate concentration, e.g., about 0.3 percent by weight, based on sugar, is preferred as previously indicated. The preferred reaction temperatures are the same in either case, i.e., 80°–85° C. followed by 140° C. Longer reaction times are required at the lower sodium carbonate concentration; this results in greater operating costs.

Various modifications can be made in the process of the present invention. According to one modification, an acid is added to the reaction mixture between the first and second hydrogenation stages, so that the second stage is conducted in a slightly acidic medium. Common mineral and organic acids of strong to moderate acid strength, such as sulfuric, hydrochloric, phosphoric, acetic, oxalic, and citric acids, can be used. The second stage hydrogenation temperatures used in this mode of operation are in the range of about 140° to about 160° C. This mode of operation is especially useful when there is a higher than average disaccharide content in the sugar mixture which undergoes hydrogenation, since an acidic medium is useful in hydrolyzing disaccharides to monosaccharides. This mode of operation is most useful when the disaccharide content exceeds about 0.5% by weight on the dry basis. When the disaccharide content is lower than about 0.5% by weight, it is ordinarily preferable to carry out the second stage of hydrogenation without the addition of acid, as previously described, since the use of acid increases the ion exchange load and requires slightly higher hydrogenation temperatures.

Mixtures of glucose, mannose, and fructose can also be used as starting materials. Such mixtures can be obtained by epimerizing glucose to a mixture of glucose and mannose in aqueous solution as previously described, and treating the glucose-mannose solution or epimerizate with glucose isomerase enzyme under conditions suitable for isomerization of part of the glucose to fructose. The resulting mixture of glucose, fructose, and mannose in aqueous solution can then be hydrogenated according to this invention as previously described, giving products containing up to about 50 percent mannitol (dry basis). An advantage of this mode of operation is that enhanced yields of mannitol are obtained. Suitable conditions for isomerization of glucose using glucose isomerase enzyme are well known in the art. A preferred procedure is to pass a solution of glucose and mannose through a column of Arthrobacter cells which have been flocculated, dried, and pelleted as described in U.S. Pat. No. 3,821,086, and then activated, as for example by soaking the dried pelleted cells in glucose-mannose solution which may contain a low concentration (e.g., about 0.004 M) of magnesium ions. The sugar solution after epimerization and enzymatic isomerization typically contains about 25–32% mannose, approximately 25–30% fructose, balance principally glucose, all on the dry basis; actual amounts may be greater or smaller.

Neither glucose nor mannose in pure form is a suitable starting material for hydrogenation according to the present process. When glucose is hydrogenated under the conditions described herein, the percentage of mannitol in the resulting hydrogenation product is too low to be of economic interest. Instead, glucose should be converted by epimerization (which may be followed by enzyme isomerization) as indicated herein, to a sugar mixture which contains mannose in addition to glucose, and the resulting sugar mixture hydrogenated. Sugar mixtures containing a major amount (i.e., more than about 50% by weight dry basis) of mannose are not ordinarily suitable starting materials, because the amount of mannitol lost through isomerization of mannose in such mixtures in general exceeds the amount of mannitol gained through isomerization of glucose.

Hydrogenation and isomerization of sugars present in the starting mixture take place simultaneously in the practice of the present invention. Glucose is isomerized in part to fructose, and the resulting fructose is hydrogenated to approximately equal amounts of sorbitol and mannitol while the unconverted glucose is hydrogenated almost entirely to sorbitol. Hydrogenation of sugar mixtures (except those containing major amounts of mannose) according to the present invention results in sorbitol-mannitol mixtures containing appreciably larger amounts of mannitol than the amounts of mannitol which would be obtained by hydrogenation of the same sugar mixtures under non-isomerizing (i.e., neutral or mildly acid) conditions.

A major advantage of the hydrogenation process of this invention is that quantities of impurities formed in the present hydrogenation process are quite low compared to the amounts of impurities formed either in prior art alkaline hydrogenation processes, such as those described in U.S. Pat. Nos. 3,329,729 and 3,763,246 cited supra, or in processes in which sodium hydroxide is used instead of sodium carbonate as the alkaline agent, while at the same time there is a substantial increase in mannitol yield compared to that obtained under non-isomerizing hydrogenation conditions.

Another advantage of the process of this invention is that ion exchange loads tend to be less than the ion exchange loads when sodium hydroxide is used as the alkaline agent. Both improvement of product quality and lower ion exchange load stem from the fact that the amount of sodium carbonate or other alkaline reacting salt required for optimum operation of the present process is lower than the amount of sodium hydroxide required for optimum operation of processes employing sodium hydroxide as the alkaline agent.

This invention will be described in greater detail with respect to the examples which follow. The hydrogenation catalyst is nickel on kieselguhr, containing about 20% by weight Ni and prepared as described in U.S. Pat. No. 3,705,199, unless otherwise indicated. All percentages are by weight unless otherwise indicated.

EXAMPLE 1

Epimerization (Preparation of Starting Material)

An aqueous glucose solution, 68 percent by weight of glucose based on total solution weight, and 0.25 percent by weight of molybdic acid based on glucose, and having a pH of about 4, is heated in an air atmosphere at atmospheric pressure to 95° C., and is maintained at the temperture for 3 hours. A brown epimerized glucose product, or epimerizate is obtained.

The epimerizate is diluted to about 60 percent solids and is purified by successive treatments with "Duolite S-30" decolorizing resin, "Permutit Q-4" cation exchange resin, "Amberlite XE-275" anion exchange resin and "Darco S-51" activated carbon, and then again with "Permutit Q-4" and "Amberlite XE-275" resins. The purified epimerizate contains about 55 percent by weight of sugar solids and contains about 31 percent mannose, 64 percent glucose, and 1.3 percent disaccharides, all on the dry basis.

Hydrogenation

A portion of the purified glucose-mannose solution (55 percent solids; 31 percent mannose dry basis) prepared as described above is charged to an autoclave. To this solution are added 0.25 percent, based on sugar, of sodium carbonate (dry basis) and reduced supported nickel catalyst in an amount equivalent to 0.6 percent by weight of Ni based on sugar. The pH of the resultant slurry (feed pH) is 8.3. The autoclave contents are pressured with hydrogen at room temperature to a pressure of about 1500 psig., heated to 85° C. with a resultant pressure rise to approximately 1750 psig. maintained at 85° C. for 1.75 hours (the first stage), and then heated to 140° C. and maintained at this temperature for 0.5 hours (the second stage). The reaction product is then filtered to separate the catalyst and is cooled to room temperature. The pH of the cooled reaction product is 6.4. Analysis of the reaction product by gas liquid chromatography (GLC) shows 40.2 percent mannitol, 58.0 percent sorbitol, 0.7 percent non-sugar impurities, 0.07 percent reducing sugar, and 0.92 percent total sugar. The amounts of organic acids (e.g., gluconic acid) and their salts in the reaction product are small, as indicated by a high total accountability. Total accountability refers to the percentage of organic material in the reaction product that is accounted for by analysis. Since organic acids and their salts are the principal organic materials in the product that are not determined by the analytical procedure used, high total accountability indicates that organic acids and their salts are present in only small amounts.

This run is a good run from the standpoints of mannitol yield and product purity.

EXAMPLE 2

Glucose is epimerized and the epimerizate purified as in Example 1.

The hydrogenation procedure is the same as that in Example 1, except that the feed contains 0.3 percent of sodium carbonate based on sugar, the feed pH is 8.6, the hydrogenation temperatures are 85° C. in the first stage and 130° C. in the second stage, and the first and second stage hydrogenation times are 2.0 hours and 0.25 hour, respectively. A product containing 43.0 percent mannitol and 1.4% nonsugar impurities, both on the dry basis, is obtained.

EXAMPLES 3 to 5

Epimerization

Glucose in aqueous solution (70 percent solids) containing 0.33 percent molybdic acid is epimerized at 90° C. for 3 hours. The epimerizates used in Examples 3 and 4 are purified as in Example 1, except that "Duolite C-25" strongly acid cation exchange resin is substituted for "Permutit Q-4" resin. The epimerizate used in Example 5 is purified in the same manner except that treatment with the second portions of cation and anion exchange resins is omitted. The purified epimerizates contain about 26 percent mannose and 0.1 percent disaccharides on the dry basis.

Hydrogenation

Epimerizate prepared as described above (55 percent solids; 26 percent mannose dry basis), sodium carbonate (0.45 percent by weight, based on sugar), and supported nickel catalyst (0.6 percent Ni, based on sugar) are charged to an autoclave under nitrogen atmosphere. The reagent/catalyst slurry is pressured with hydrogen as in Example 1, and is heated in two stages to the temperatures and for the times indicated in Table 1. The reaction product is filtered, cooled, and analyzed as in Example 1. Results are shown in Table 1 below.

TABLE 1

| Example | 3 | 4 | 5 |
|---|---|---|---|
| Feed: | | | |
| % Na$_2$CO$_3$ (on sugar) | 0.45 | 0.45 | 0.45 |

TABLE 1-continued

| Example | 3 | 4 | 5 |
|---|---|---|---|
| % Ni (on sugar) | 0.6 | 0.6 | 0.6 |
| pH at start | 9.0 | 8.8 | 8.7 |
| 1st stage hydrog.,: | | | |
| Temp., °C. | 85 | 90 | 95 |
| Time, hr. | 1.6 | 1.6 | 1.6 |
| 2nd stage hydrog. | | | |
| Temp., °C. | 140 | 140 | 140 |
| Time, hr. | 0.4 | 0.4 | 0.4 |
| Final pH | 6.9 | 6.8 | 6.8 |
| Product (d.b.): | | | |
| Mannitol | 34.6 | 36.9 | 37.7 |
| Total Sugar | 0.5 | 0.5 | 0.5 |

These examples show that the percentage of mannitol in the reaction product increases as first stage reaction temperature is raised. However, the amounts of side products (e.g., organic acids) which are not accounted for by analysis are higher in Example 5 than in Examples 3 and 4.

EXAMPLES 6 AND 7

Epimerization and purification are carried out as in Example 3. The epimerizate contains about 26 percent mannose, and 0.1% disaccharides.

Hydrogenation is carried out as in Example 1, except that sodium carbonate and catalyst quantities, reaction conditions, and product analysis are as shown in Table 2 below. The amount of sodium carbonate in each of these examples is 0.60 percent by weight, based on sugar.

TABLE 2

| Example | 6 | 7 |
|---|---|---|
| Na$_2$CO$_3$ (on sugar) | 0.60 | 0.60 |
| % Ni (on sugar) | 0.6 | 0.6 |
| pH at start | 9.1 | 9.0 |
| 1st stage: | | |
| Temp., °C. | 80 | 90 |
| Time, hr. | 1.6 | 1.6 |
| 2nd stage: | | |
| Temp., °C. | 140 | 140 |
| Time, hr. | 0.4 | 0.4 |
| Final pH | 7.7 | 7.2 |
| Product (d.b.): | | |
| Mannitol | 40.4 | 38.5 |
| Total Sugar | 0.5 | 0.5 |

Comparison of Examples 6 and 7 with Examples 3–5 suggests that the use of higher sodium carbonate concentrations leads to higher percentages of mannitol in the product. In Examples 3–7 the amount of mannitol produced and the total sugar left in the product are less than in Example 2. This is a result of the milder epimerization conditions producing less mannose and less disaccharides.

EXAMPLES 8 to 11

Epimerization and purification are carried out as in Example 1, yielding epimerized glucose containing 31 percent mannose on the dry basis.

Epimerized glucose (55 percent solids; 31 percent mannose dry basis) prepared as described above, nickel catalyst equivalent 0.6 percent Ni based on sugar, and sodium carbonate, and sodium bicarbonate in the amounts indicated in Table 3 below, are charged to an autoclave under nitrogen atmosphere. Reaction temperatures and times are as shown in Table 3, and acetic acid is added between the first and second hydrogenation stages in Examples 9 and 11; otherwise hydrogenation procedures are similar to those of Example 1. The reaction products in Examples 9 and 11 are treated in a mixed bed of ion exchange resins (40 percent by weight of "Permutit Q" strongly acid cation exchange resin and 60 percent by weight of "Permutit S-2" strongly basic anion exchange resin) prior to analysis. Amounts of mannitol in the product are given in Table 3.

TABLE 3

| Example | 8 | 9 | 10 | 11 |
|---|---|---|---|---|
| Feed: | | | | |
| % Na$_2$CO$_3$ (on sugar) | 0.25 | 0.23 | 0.5 | 0.46 |
| % NaHCO$_3$ (on sugar) | 0.5 | 0.46 | 1.0 | — |
| % Ni (on sugar) | 0.6 | 0.6 | 0.6 | 0.6 |
| pH at start | 8.4 | 8.4 | 8.6 | 9.1 |
| 1st stage hydrog: | | | | |
| Temp., °C. | 80 | 80 | 80 | 80 |
| Time, hr. | 2.0 | 2.0 | 2.0 | 2.0 |
| 2nd stage hydrog.: | | | | |
| % Acetic Acid (on sugar) | — | 0.46 | — | 0.46 |
| Temp. °C. | 120 | 150 | 120 | 150 |
| Time, hr. | 0.25 | 0.5 | 0.25 | 0.5 |
| Final pH | 7.3 | 5.4 | 8.1 | 5.0 |
| Product (d.b.): | | | | |
| Mannitol | 41.4 | 35.4 | 44.2 | 38.2 |
| Reducing Sugar | 0.34 | 0.07 | 0.12 | 0.07 |
| Total Sugar | 1.14 | 0.50 | 0.83 | 0.53 |
| Accountability | 100.5 | 100.3 | 98.6 | 100.2 |

An exceptionally high product mannitol percentage is achieved in Example 10; however, an exceptionally heavy load is imposed on ion exchange resins used to deionize the product because of the large amounts of sodium salts used. Example 8 yields a product having a good mannitol percentage, and a high purity (except for sugar), with an ion exchange load about half that of Example 10. A high reducing sugar value (0.34 percent) in Example 8 shows incomplete reduction, which can be remedied by a higher second stage hydrogenation temperature in the presence of acetic acid as in Example 9. Example 11 also illustrates a two stage hydrogenation process in which the first stage is carried out under alkaline conditions and the second stage under acid conditions using added acid. A higher second stage temperature is permissible because of the acidic medium. The addition of acid prior to second stage hydrogenation is not ordinarily preferred except when the epimerized glucose feed contains a significant quantity (about 0.5 percent or more) of disaccharides or when a reduced residence time in the second stage is desirable.

EXAMPLE 12

Glucose in aqueous solution is epimerized as in Example 1 and is treated with "Duolite S-30" decolorizing resin, a cation exchange resin (Permutit Q-4), an anion exchange resin ("Amberlite XE-275"), and with "Darco S-51" decolorizing carbon, giving a purified glucose epimerizate containing 28 percent by weight mannose.

A feed slurry comprising epimerized glucose (55 percent solids; 28 percent mannose dry basis), nickel catalyst (0.6 percent Ni based on sugar), and 0.6 percent by weight of added sodium carbonate, based on sugar, and having an initial pH of 9.0, is passed continuously through a four reactor system in which the reactors are arranged in series. The temperature in the first three reactors is 90° C. and the temperature in the final reactor is 140° C. The flow rate is such as to give a total residence time of 2.5 hours (2.0 hours at 90° C. and 0.5 hour at 140° C.). A product containing 39.3 percent mannitol, 0.09 percent reducing sugar and 0.48 percent total sugar, all on the dry basis, is obtained.

EXAMPLE 13

Glucose in aqueous solution is epimerized and purified to give 28 percent mannose on the dry basis.

The above epimerized glucose solution, containing 0.004 M magnesium ion (as magnesium chloride) and adjusted to a pH of 8.2-8.5, is passed downwardly through a column of dried pelleted Arthrobacter cells containing glucose isomerase at 60° C. The cells are prepared as described in U.S. Pat. No. 3,821,086 and are activated by swelling in a solution containing 0.1 M NaHCO$_3$ and 0.01 M MgCl$_2$ and washed in 0.004 M MgCl$_2$ prior to use. The column effluent contains about 27 percent mannose, 25 percent fructose, and 46 percent glucose, all on the dry basis. This effluent is purified by treatment with anion and cation exchange resins (i.e., Permutit Q-4 and Amberlite IRA-68 resins).

A feed containing a solution of glucose, fructose, and mannose prepared as described above (55 percent solids), nickel catalyst equivalent to 0.6 percent Ni based on sugar, and 0.3 percent by weight of added sodium carbonate, and having a pH of 8.7 is hydrogenated at 85° C. for 2.0 hours, then 130° C. for 0.25 hour. The product contains 47.1 percent mannitol and 50.1 percent sorbitol, both on the dry basis.

EXAMPLE 14

Glucose is epimerized by heating an aqueous solution containing about 60 percent glucose and 0.25 percent, based on the dry weight of glucose, of molybdic acid to 95° C. maintaining the solution at this temperature for 3 hours, and cooling the solution. The resulting dark brown epimerized glucose solution, or epimerizate, is treated with a cation exchange resin ("Permutit Q") and a weakly basic anion exchange resin ("Amberlite XE-275", Rohm & Haas Co., Philadelphia, Pa.) and with 2%, based on sugar, of "Darco S-51" (ICI Americas Inc., Wilmington, Del.) decolorizing carbon, giving a decolorized and essentially molybdenum free (less than 1 ppm Mo) aqueous solution of glucose and mannose, containing about 30% by weight of mannose and about 70% by weight of glucose on the dry basis.

The purified epimerized glucose solution (200 ml.; 120 g. or 60% by weight sugar solids; 30% mannose and 70% glucose dry basis), 1.5 g of sodium carbonate (1.25% by weight, based on sugar), and 5 g. of nickel on kieselguhr catalyst (1 g., or 0.8% based on sugar, of Ni) are charged to an autoclave under a nitrogen atmosphere. The pH of this mixture is 9.6. The autoclave is pressured with hydrogen to 1500 psig., heated to 80° C., and maintained at this temperature for 2 hours. The reaction product slurry is cooled to room temperature and filtered; the filtrate pH is 9.2. The filtrate is treated with a mixed bed ion exchange resin (i.e., a bed containing an anion exchange resin and a cation exchange resin) and with "Darco S-51" decolorizing carbon, giving a clear solution containing about 42.7% mannitol on the dry basis. However, the amounts of impurities are significantly higher than the amount obtained when using smaller amounts of sodium carbonate in two stage operation as previously described.

EXAMPLE 15

A glucose epimerizate solution containing 26.8% by weight of mannose on the dry basis and 0.3% by weight of added sodium carbonate and having an initial pH of 8.8, is hydrogenated in the presence of a nickel catalyst (0.6% Ni based on sugar) at 85° C. for 2 hours, then at 130° C. for 0.25 hour. A product containing 36.0% mannitol, 0.1% reducing sugar, 0.8% total sugar, and 1.0% impurities, all on the dry basis, is obtained.

EXAMPLE 16

A glucose epimerizate solution containing 26.8% by weight (dry basis) of mannose and 0.28% by weight (based on sugar weight) of added trisodium phosphate and having an initial pH of 8.7, is hydrogenated in the presence of a nickel catalyst (0.6% Ni based on sugar) at 95° C. for 1.6 hours, then at 140° C. for 0.4 hour. The product contains 34.7% mannitol, 0.1% reducing sugar, 0.9% total sugar, and 0.9% impurities, all by weight on the dry basis.

Comparison of this example with Example 15 shows that slightly higher temperatures are required and that mannitol yields are slightly lower than trisodium phosphate is used in place of sodium carbonate at a concentration giving essentially the same alkalinity. This suggests the sodium phosphate is a useful alkaline agent, although probably not as good as sodium carbonate, for obtaining enhanced mannitol yields with low impurities contents.

EXAMPLE 17

A decolorized and deionized aqueous glucose-mannose solution containing 27.1% by weight of mannose on the dry basis was made alkaline by the addition of 0.30% by weight of sodium carbonate, based on the weight of sugar. The resulting alkaline solution, having a pH of 8.8, was hydrogenated in the presence of a nickel catalyst (0.6% Ni based on sugar) at 85° C. for 2.0 hours, then at 130° C. for 0.25 hour. The final pH of the solution, after reaction, cooling, and separation of the catalyst, was 6.8. Analysis of the product showed 35.8% mannitol, 0.4% impurities other than sugars, 0.1% reducing sugar, and 0.6% total sugar, all by weight of the dry basis.

EXAMPLES 18 TO 20

Portions of a decolorized and deionized glucose-mannose epimerizate solution containing 27.1% by weight (dry basis) mannose were made alkaline by the addition of trisodium phosphate in the amounts shown in Table 4 below. These solutions were hydrogenated in the presence of a nickel catalyst (0.6% Ni based on sugar) at the temperatures and for the times shown in Table 4 below. The final pH of each solution, and the analysis of each product on the dry basis, are also shown in Table 4 below.

TABLE 4

| EXAMPLE | 18 | 19 | 20 |
|---|---|---|---|
| % Na$_3$PO$_4$ (on sugar) | 0.33 | 0.38 | 0.38 |
| pH at start | 8.9 | 8.9 | 8.9 |
| 1st stage: | | | |
| Temp., °C. | 85 | 85 | 95 |
| Time, hr. | 2.00 | 2.00 | 1.60 |
| 2nd stage: | | | |
| Temp., °C. | 130 | 130 | 140 |
| Time, hr. | 0.25 | 0.25 | 0.40 |
| Final pH | 6.2 | 6.3 | 5.7 |
| Product (d.b.): | | | |
| Mannitol | 34.5 | 34.7 | 34.7 |
| Non-sugar impurities | 0.3 | 0.3 | 0.3 |
| Reducing sugar | 0.2 | 0.1 | 0.1 |
| Total sugar | 0.7 | 0.6 | 0.5 |

COMPARATIVE EXAMPLE A

A comparison run, was carried out under the same conditions as Example 2 except that 0.3 percent by weight of sodium hydroxide (based on sugar) is used in place of sodium carbonate, giving a feed pH of 9.6. A mannitol yield of 42.9 percent is obtained, and reducing sugar (0.13 percent) is acceptable. However, non-sugar impurities found by analysis (3.6 percent, including 1.9 percent isomers), and impurities not accounted for by analysis are greater than in Example 2. This indicates that sodium hydroxide is a less desirable alkaline material than sodium carbonate when operating at low alkaline material levels.

COMPARATIVE EXAMPLE B

A comparison run was carried out under the same conditions as Example 2 except that no alkaline agent was used, giving a feed pH of 7.5. The product obtained on hydrogenation contains 32.9% mannitol and 0.7% impurities, both on the dry basis. Comparison of this example with examples according to the present invention, particularly Example 2, shows that considerable enhancement in mannitol yield is obtained without excessive impurities formation by hydrogenating in the presence of an alkaline reacting alkali metal salt according to the present invention.

What is claimed is:

1. A process for preparing a mannitol-rich solution of sorbitol and mannitol which comprises hydrogenating an aqueous epimerizate solution comprising glucose and mannose with hydrogen in the presence of a hydrogenation catalyst at a temperture from about 60° to about 100° C., said epimerizate solution containing an alkali metal salt of a weak acid in sufficient quantity to impart an initial pH from about 8 to about 10, so that the percentage of mannitol in said mannitol-rich solution exceeds the percentage of mannitol which would be obtained from hydrogenation of said epimerizate solution under non-isomerizing conditions.

2. A process according to claim 1 in which said epimerizate is obtained by catalytic epimerization of glucose.

3. A process according to claim 1 in which the amount of said alkali metal salt is sufficient to impart an initial pH of about 8 to about 9 to said solution.

4. A process according to claim 1 in which said alkali metal salt is sodium carbonate.

5. A process according to claim 1 in which said alkali metal salt is trisodium phosphate.

6. A process according to claim 4 in which the amount of sodium carbonate is sufficient to impart an initial pH of about 8 to about 9 to said solution.

7. A process according to claim 4 in which the amount of sodium carbonate is from about 0.2% to about 1.5% by weight, based on sugar.

8. A process according to claim 4 in which the amount of sodium carbonate is from about 0.25% to about 0.8% by weight, based on sugar.

9. A process according to claim 4 in which said solution also contains sodium bicarbonate.

10. A process according to claim 1 in which said epimerizate is a glucose isomerase enzyme-treated epimerizate containing glucose, mannose, and fructose and is obtained by catalytic epimerization of glucose and treatment of the resulting solution with glucose isomerase enzyme.

11. A process according to claim 1 in which hydrogenation is carried out in two stages, the first stage being carried out at a temperature in the range of about 60° to about 100° C., the second stage being carried out at a temperature in the range of about 110° C. to about 160° C.

12. A process according to claim 11 in which said solution at the start of hydrogenation contains about 0.25% to about 0.8% by weight, based on sugar, of sodium carbonate.

* * * * *